United States Patent [19]

Schuda et al.

[11] Patent Number: 4,876,364

[45] Date of Patent: * Oct. 24, 1989

[54] HYDROGENATION PROCESS FOR THE FORMATION OF 4A,5-DIHYDRO HMG-COA REDUCTASE INHIBITORS

[75] Inventors: Ann D. Schuda, New Providence; Thomas R. Verhoeven, Cranford; Ichiro Shinkai, Westfield, all of N.J.

[73] Assignee: Merck & Co., Inc., Rahway, N.J.

[ * ] Notice: The portion of the term of this patent subsequent to Sep. 5, 2006 has been disclaimed.

[21] Appl. No.: 92,802

[22] Filed: Sep. 3, 1987

[51] Int. Cl.$^4$ ............................................ C07D 309/30
[52] U.S. Cl. ...................................... 549/214; 549/292
[58] Field of Search ................................. 549/214, 292

[56] References Cited

U.S. PATENT DOCUMENTS 4,490,546  12/1984  Kuo ..................................... 549/292

OTHER PUBLICATIONS

Schrock et al, "Catalytic hydrogenation using, etc" CA 85:123066 D (1976).
Santos et al, "Catalytic activity and Visible, etc" CA 100:180758t (1984).
Crabtree et al I, "Cationic Iridiun dialefin, etc" CA 88:31361q (1978).
Kuo et al., *J. Org. Chem.*, 48, 1991 (1983).
Evans et al., *J. Am. Chem. Soc.*, 106, 3866 (1984).
Crabtree et al., *Organometallics*, 2, 682 (1983).

*Primary Examiner*— Raymond
*Attorney, Agent, or Firm*—Melvin Winokur; Joseph F. DiPrima

[57] ABSTRACT

A novel hydrogenation process, employing an iridium or rhodium catalyst, in an alcoholic solvent mixture, for the reduction of the 4a,5 double bond in the polyhydronaphthyl ring of des-(α-methylbutyryl)-8-hydroxy-lovastatin or analogs thereof, is disclosed.

18 Claims, No Drawings

HYDROGENATION PROCESS FOR THE FORMATION OF 4A,5-DIHYDRO HMG-COA REDUCTASE INHIBITORS

BACKGROUND OF THE INVENTION

Lovastatin and derivatives derived therefrom (e.g. Simvastatin) are potent HMG-CoA reductase inhibitors. Lovastatin is produced in fermentations with *Aspergillus terreus* as described in U.S. Pat. No. 4,231,938 by Monaghan et al. A 4a,5-dihydrolovastatin (I) is co-produced with lovastatin in considerably

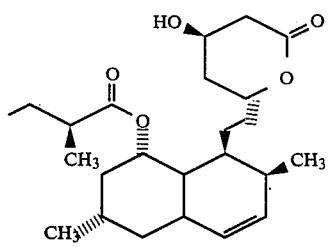

lower yield as described in U.S. Pat. No. 4,294,846 by Albers-Schonberg et al. However, this naturally occurring 4a,5-dihydromevinolin appears to be slightly more active than lovastatin as an HMB-CoA reductase inhibitor. Efforts to convert the more abundant lovastatin to its more active 4a,5-dihydro derivative have been made by catalytic reduction as reported in published EP application No. 0033537 but no evidence of the desired trans-fused 4a,5-dihydrolovastatin was found.

Kuo et al. (U.S. Pat. No. 4,490,546 and J. Org. Chem. 48, 1991 (1983)) have disclosed a process for hydrogenating the 4a,5 double bond of lovastatin. However this process requires 5 separate steps leading to the natural trans isomer in about 10 percent yield. Moreover the desired product is contaminated with the cis-fused dihydro derivative.

The use of a ligating group, such as OH, on an olefinic substrate is known to direct the attack of a hydrogenation catalyst such as [Ir(COD)PCy$_3$(pyr)]PF$_6$ from the face of the moleule containing the directing group. However, there are no reports of selective hydrogenation of a conjugated diene, with catalysts of this type.

DETAILED DESCRIPTION OF THE INVENTION

The novel process of this invention may be depicted as:

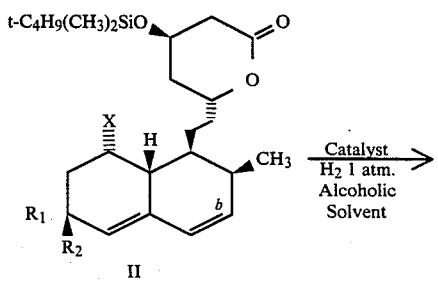

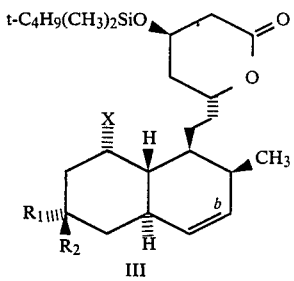

wherein

X is OH, NH$_2$ or OR; where R is C$_{1-5}$alkyl, C$_{3-7}$cycloalkyl, phenylC$_{1-3}$alkyl, or substituted phenylC$_{1-3}$alkyl in which the substituent is halogen, CF$_3$ or CN;

R$_1$ is H or CH$_3$ or CH$_2$OSi(Me)$_2$t—C$_4$H$_9$ or OSi(Me)$_2$t—C$_4$H$_9$;

R$_2$ is H or CH$_2$OSi(Me)$_2$t—C$_4$H$_9$ or OSi(Me)$_2$t—C$_4$H$_9$; provided that when R$_1$ or R$_2$ is CH$_2$OSi(Me)$_2$t—C$_4$H$_9$ the other is H; and one and only one of R$_1$ and R$_2$ can be OSi(Me)$_2$t—C$_4$H$_9$.

Alternatively R$_1$ and R$_2$ may be represented as:
R$_1$ is H or CH$_3$ or CH$_2$OSi(Me)$_2$t—C$_4$H$_9$;
R$_2$ is H or CH$_2$OSi(Me)$_2$t—C$_4$H$_9$; provided that at least one of R$_1$ or R$_2$ is H.

The catalyst is [Ir(COD)PCy$_3$(pyr)]PF$_6$ or [Rh(NBD)(DIPHOS-4)]BF$_4$ The alcoholic solvent is a mixture of dichloromethane, chloroform or chlorobenzene or a like substance and an alcohol such as isopropanol or ethanol; b is a double bond or single bond.

Tert-butyldimethylsilyl is shown as a hydroxyl protecting group. It will be clear to those skilled in the art that other hydroxyl protecting groups such as tert-butyldiphenylsilyl, trimethylsilyl, triethylsilyl, triisopropylsilyl and tetrahydropyranyl could be substituted for tert-butyldimethylsilyl without affecting the outcome of the instant invention.

The reduced product (III) wherein X is OH can be readily modified through esterification of the C-8 hydroxyl group and removal of protecting groups to yield a variety of 8-acyloxy derivatives. This esterification can be accomplished following the acylation procedure disclosed by Hoffman et al. U.S. Pat. No. 4,444,784 or that described in copending U.S. application Ser. No. 038580 filed Apr. 15, 1987.

Products (III) wherein X is NH$_2$ can be converted into 8-amido derivatives following the procedure exemplified in U.S. Pat. No. 4,472,426. The 8-amido derivatives are disclosed in the above patent as HMG-CoA reductase inhibitors.

Products (III) wherein X is OR are disclosed in U.S. Pat. No. 4,282,155 as HMG-CoA reductase inhibitors.

The instant process selectively reduces the 4a,5 double bond in the polyhydronaphthyl ring of des-(α-methylbutyryl)-8-hydroxy lovastatin or analogs thereof. In this reduction, the C-8 hydroxyl, or a comparable ligating group such as OR or NH$_2$ is utilized to direct the delivery of hydrogen to the more sterically hindered 4a,5 double bond. The agent used to effect this directed hydrogen transfer is a homogenous iridium or rhodium catalyst. Critical to the present invention is the utilization of an alcoholic cosolvent to modify catalyst activity and thus minimize formation of a tetrahydro derivative. The inclusion of an alcoholic cosolvent in the reaction mixture increases the ratio of product to tetrahydro derivative from 3:2 to 9:1. The instant process yields a single dihydro product. No dihydro products derived from reduction of the 3,4 double bond are observed; furthermore, double bond isomerization which could lead to formation of the 4,4a double bond is not observed.

One embodiment of the present invention is the preparation of compounds of structure (III) wherein X is OH and b is a double bond. This embodiment is exemplified by compounds wherein:

a. $R_1=CH_3$, $R_2=H$;

b. $R_1=CH_2OSi(Me)_2t-C_4H_9$, $R_2=H$;

c. $R_1=H$, $R_2=CH_2OSi(Me)_2t-C_4H_9$;

d. $R_1=OSi(Me)_2t-C_4H_9$, $R_2=H$;

e. $R_1=H$, $R_2=OSi(Me)_2t-C_4H_9$;

f. $R_1=CH_3$, $R_2=OSi(Me)_2t-C_4H_9$.

A second embodiment of the present invention is the preparation of compounds of structure (III) wherein X is $NH_2$. This embodiment is exemplified by compounds wherein:

a. $R_1=CH_3$, $R_2=H$;

b. $R_1=CH_2OSi(Me)_2t-C_4H_9$, $R_2=H$;

c. $R_1=H$, $R_2=CH_2OSi(Me)_2t-C_4H_9$.

d. $R_1=OSi(Me)_2t-C_4H_9$, $R_2=H$;

e. $R_1=H$, $R_2=OSi(Me)_2t-C_4H_9$;

f. $R_1=CH_3$, $R_2=OSi(Me)_2t-C_4H_9$.

A third embodiment of the present invention is the preparation of compounds of structure (III) wherein X is OR. In one class of this embodiment R is $CH_3$ or p-fluorobenzyl. This class is exemplified by compounds wherein:

a. $R=CH_3$, $R_1=CH_3$, $R_2=H$;

b. $R$=p-fluorobenzyl, $R_1=CH_3$, $R_2=H$;

c. $R=CH_3$, $R_1=CH_2OSi(Me)_2t-C_4H_9$, $R_2=H$;

d. $R$=p-fluorobenzyl, $R_1=CH_3$, $R_2=H$;

e. $R=CH_3$, $R_1=H$, $R_2=CH_2OSi(Me)_2t-C_4H_9$;

f. $R$=p-fluorobenzyl, $R_1=H$, $R_2=CH_2OSi(Me)_2t-C_4H_9$;

g. $R=CH_3$, $R_1=OSi(Me)_2t-C_4H_9$, $R_2=H$;

h. $R$=p-fluorobenzyl, $R_1=OSi(Me)_2t-C_4H_9$, $R_2=H$;

i. $R=CH_3$, $R_1=H$, $R_2=OSi(Me)_2t-C_4H_9$;

j. $R$=p-fluorobenzyl, $R_1=H$, $R_2=OSi(Me)_2t-C_4H_9$;

k. $R=CH_3$, $R_1=CH_3$, $R_2=OSi(Me)_2t-C_4H_9$;

l. $R$=p-fluorobenzyl, $R_1=CH_3$, $R_2=OSi(Me)_2t-C_4H_9$.

Starting olefin wherein X is OH and $R_1$ is $CH_3$ is readily prepared from lovastatin following the hydrolysis conditions disclosed in U.S. Pat. No. 4,444,784. The 4-hydroxy function in the lactone moiety is protected with a suitable protecting agent, exemplified here as a t-butyldimethylsilyl group, according to the procedure disclosed in U.S. Pat. No. 4,444,784. Starting olefins wherein X is OH and $R_1$ or $R_2$ is $CH_2OSi(Me)_2t-C_4H_9$ are prepared following the procedure outlined in co-pending U.S. patent application Ser. No. 048136 filed May 15, 1987, followed by protection with $t-C_4H_9(Me)_2SiCl$.

Starting olefins wherein X is OR can be prepared following the procedure described in U.S. Pat. No. 4,282,155; where X is $NH_2$ the olefins can be prepared following the procedure in U.S. Pat. No. 4,472,426.

Starting olefins where $R_1$ or $R_2$ is $OSi(Me)_2t-C_4H_9$ can be prepared following the descriptions in U.S. Pat. Nos. 4,517,373 and 4,537,859 for preparing the 6-hydroxyl derivatives followed by protection with $t-C_4H_9(Me)_2SiCl$.

The iridium catalyst $Ir[(COD)PCy_3(pyr)]PF_6$. (COD=1,5-cyclooctadiene, $PCy_3$=tricyclohexylphosphine, pyr=pyridine) can be prepared following the procedure of Crabtree et al., *J. Organomet. Chem.*, 135, 395 (1977). The rhodium catalyst [Rh(NBD)(DIPHOS-4)]$BF_4$ (NBD=norbornadiene, DIPHOS-4=1,4-bis(diphenylphosphino)butane) can be prepared following the procedure described by Stille et al. *J. Org. Chem.* 47., 468 (1982) and further detailed by Evans et al. reported in *J. Am. Chem. Soc.*, 106, 3866 (1984). The hydrogenation procedure described herein may use the above described iridium or rhodium catalyst or a like catalyst capable of complexing with the C-8 hydroxyl, ether or amino functionality; the preferred catalyst is the iridium catalyst. The relative mole percent of catalyst to olefinic substrate may be 0.1 to 10 mole percent, preferably about 2.5 mole percent.

The alcoholic solvent for the instant process is a mixture of dichloromethane, chloroform or chlorobenzene or a like substance and a lower alkyl chain alcohol such as ethanol or isopropanol. The preferred mixture is dichloromethane and isopropanol. The relative proportions of halogenated hydrocarbon to alcohol may be about 20:1 to about 2:1 by volume, preferably about 6:1. The relative ratio of equivalents of alcohol to equivalent olefin is 0.5:1 to 10:1, preferably 3:1.

The olefinic substrate and catalyst are dissolved in the solvent and the mixture reduced under atmospheric hydrogen pressure at ambient temperature for about 20 hours. The reaction mixture is worked up following standard procedures to yield a 9:1 mixture of the 4a,5-dihydro to trans tetrahydro derivative. Further purification is accomplished by chromatography of this mixture; where X is OH, the hydroxyl group may first be acylated and then flash chromatographed with a 25% by volume ethyl acetate:hexane mixture.

The following Examples illustrate the present invention and as such are not to be considered as limiting the invention set forth in the claims appended hereto.

EXAMPLE 1

Preparation of 6(R)-[2-8(S)-hydroxy-2(S),6(R)-dimethyl-1,2,4a(R),5,6,7,8,8a(S)-octahydro-1(S)]ethyl]-4(R)-tert-butyldimethylsilyloxy-3,4,5,6-2H-pyran-2-one.

A solution of 6(R)-[2-[8(S)-hydroxy-2(S),6(R)-dimethyl-1,2,6,7,8,8a(R)-hexahydro-1(S)]-ethyl]-4(R)-tert-butyldimethylsilyloxy-3,4,5,6-2H-pyran-2-one (1.36 g, 3.12 mmol) in anhydrous dichloromethane (4.2 ml) and isopropanol (0.72 ml, 9.36 mmol) was briefly purged with argon gas. 1,5-Cyclooctadiene(pyridine)(tricyclohexylphosphine)iridium(I)hexafluorophosphate (62.5 mg, 2.5 mole percent) was added and the mixture reduced at atmospheric hydrogen pressure at ambient temperature for 21 hours.

The volatiles were removed in vacuo and the resulting solid taken up in 150 ml of warm diethyl ether, filtered (by vacuum) through a one inch bed of Florisil ® (Magnesium silicate filter aid used herein to retain any catalyst complex which remained in solution) and washed with 2×50 ml of warm diethyl ether. The volatiles were again evaporated in vacuo to give a white crystalline solid which was identified by NMR as a 9:1 mixture of the title compound to the trans tetrahydro derivative.

$^1$HNMR (300 MHz, CDCl$_3$) δ 5.62 (ddd, J=2.5, 4.9, 9.5 Hz, 1H), 5.38 (d, J=9.5 Hz, 1H), 4.67 (m, 1H), 4.29 (m, 1H), 4.17 (m, 1H), 1.0-2.1 (m, 11H), 0.85 (m, 12H), 0.06 (s, 6H).

EXAMPLES 2-24

Following essentially the procedure of Example 1 but substituting for the olefin therein, approximately equimolar amounts of the compounds of structure (II) as described below there are prepared the corresponding 4a(R),5-dihydro derivatives (III).

|  | X | R$_1$ | R$_2$ | b |
|---|---|---|---|---|
| Example 2 | OH | CH$_2$OSi(Me)$_2$t-C$_4$H$_9$ | H | db |
| Example 3 | OH | H | CH$_2$OSi(Me)$_2$t-C$_4$H$_9$ | db |
| Example 4 | NH$_2$ | CH$_3$ | H | db |
| Example 5 | NH$_2$ | CH$_2$OSi(Me)$_2$t-C$_4$H$_9$ | H | db |
| Example 6 | NH$_2$ | H | CH$_2$OSi(Me)$_2$t-C$_4$H$_9$ | db |
| Example 7 | OCH$_3$ | CH$_3$ | H | db |
| Example 8 | OCH$_3$ | CH$_2$OSi(Me)$_2$t-C$_4$H$_9$ | H | db |
| Example 9 | OCH$_3$ | H | CH$_2$OSi(Me)$_2$t-C$_4$H$_9$ | db |
| Example 10 | p-fluorobenzyloxy | CH$_3$ | H | db |
| Example 11 | p-fluorobenzyloxy | CH$_2$OSi(Me)$_2$t-C$_4$H$_9$ | H | db |
| Example 12 | p-fluorobenzyloxy | H | CH$_2$OSi(Me)$_2$t-C$_4$H$_9$ | db |
| Example 13 | OH | OSi(Me)$_2$t-C$_4$H$_9$ | H | db |
| Example 14 | OH | H | OSi(Me)$_2$t-C$_4$H$_9$ | db |
| Example 15 | OH | CH$_3$ | OSi(Me)$_2$t-C$_4$H$_9$ | db |
| Example 16 | NH$_2$ | OSi(Me)$_2$t-C$_4$H$_9$ | H | db |
| Example 17 | NH$_2$ | H | OSi(Me)$_2$t-C$_4$H$_9$ | db |
| Example 18 | NH$_2$ | CH$_3$ | OSi(Me)$_2$t-C$_4$H$_9$ | db |
| Example 19 | OCH$_3$ | OSi(Me)$_2$t-C$_4$H$_9$ | H | db |
| Example 20 | OCH$_3$ | H | OSi(Me)$_2$t-C$_4$H$_9$ | db |
| Example 21 | OCH$_3$ | CH$_3$ | OSi(Me)$_2$t-C$_4$H$_9$ | db |
| Example 22 | p-fluorobenzyloxy | OSi(Me)$_2$t-C$_4$H$_9$ | H | db |
| Example 23 | p-fluorobenzyloxy | H | OSi(Me)$_2$t-C$_4$H$_9$ | db |
| Example 24 | p-fluorobenzyloxy | CH$_3$ | OSi(Me)$_2$t-C$_4$H$_9$ | db |

What is claimed is:

1. A process for the preparation of a compound of structural formula (III):

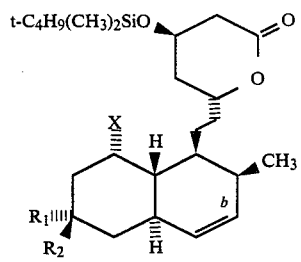

III wherein:

X is OH, NH$_2$ or OR; where R is C$_{1-5}$alkyl, C$_{3-7}$cycloalkyl, phenylC$_{1-3}$alkyl, or substituted phenylC$_{1-3}$alkyl in which the substituent is halogen, CN, or CF$_3$;

R$_1$ is H or CH$_3$ or CH$_2$OSi(Me)$_2$t—C$_4$H$_9$ or OSi(Me)$_2$t—C$_4$H$_9$;

R$_2$ is H or CH$_2$OSi(Me)$_2$t—C$_4$H$_9$ or OSi(Me)$_2$t—C$_4$H$_9$; provided that when R$_1$ or R$_2$ is CH$_2$OSi(Me)$_2$t—C$_4$H$_9$ the other is H; and one and only one of R$_1$ and R$_2$ can be OSi(Me)$_2$t—C$_4$H$_9$; and b is a double bond or a single bond;

which comprises:

contacting a compound of structural formula (II)

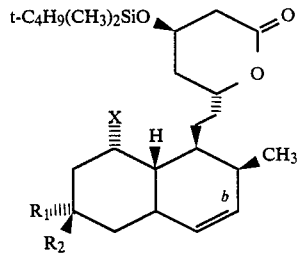

II with 1,5-cyclooctadiene(pyridine)(tricyclohexyl-phosphine)iridium(I)hexafluorophosphate or norbornadiene-1,4-bis(diphenylphosphino)butane rhodium(I)hexafluoroborate; in an alcoholic solvent, under hydrogen gas pressure.

2. A process of claim 1 wherein the catalyst is 1,5-cyclooctadiene(pyridine)(tricyclohexylphosphine)iridium(I)hexafluorophosphate.

3. A process of claim 2 wherein the alcoholic solvent is a mixture of dichloromethane, or chloroform, or chlorobenzene and ethanol or isopropanol.

4. A process of claim 3 wherein the alcoholic solvent is a mixture of dichloromethane and isopropanol.

5. A process of claim 1 wherein $R_1$ is H, or $CH_3$, or $CH_2OSi(Me)_2t$—$C_4H_9$; $R_2$ is H or $CH_2OSi(Me)_2t$—$C_4H_9$; provided that when $R_1$ or $R_2$ is $CH_2OSi(Me)_2t$—$C_4H_9$ the other is H.

6. A process of claim 1 wherein: X is OH and b is a double bond.

7. A process of claim 6 wherein the compound (III) prepared is selected from the group wherein
   a. $R_1$ is $CH_3$, $R_2$ is H,
   b. $R_1$ is $CH_2OSi(Me)_2t$—$C_4H_9$, $R_2$ is H,
   c. $R_1$ is H, $R_2$ is $CH_2OSi(Me)_2t$—$C_4H_9$,
   d. $R_1$ is $OSi(Me)_2t$—$C_4H_9$, $R_2$ is H,
   e. $R_1$ is H, $R_2$ is $OSi(Me)_2t$—$C_4H_9$,
   f. $R_1$ is $CH_3$, $R_2$ is $OSi(Me)_2t$—$C_4H_9$.

8. A process of claim 1 wherein X is $NH_2$ and b is a double bond.

9. A process of claim 8 wherein the compound (III) prepared is selected from the group wherein:

a. $R_1=CH_3$, $R_2=H$;

b. $R_1=CH_2OSi(Me)_2t$—$C_4H_9$, $R_2=H$;

c. $R_1=H$, $R_2=CH_2OSi(Me)_2t$—$C_4H_9$;

d. $R_1=OSi(Me)_2t$—$C_4H_9$, $R_2=H$;

e. $R_1=H$, $R_2=OSi(Me)_2t$—$C_4H_9$;

f. $R_1=CH_3$, $R_2=OSi(Me)_2t$—$C_4H_9$.

10. A process of claim 1 wherein X is OR and b is a double bond.

11. A process of claim 10 wherein X is $OCH_3$.

12. A process of claim 11 wherein the compound (III) prepared is selected from the group wherein:

a. $R_1=CH_3$, $R_2=H$;

b. $R_1=CH_2OSi(Me)_2t$—$C_4H_9$, $R_2=H$;

c. $R_1=H$, $R_2=CH_2OSi(Me)_2t$—$C_4H_9$;

d. $R_1=OSi(Me)_2t$—$C_4H_9$, $R_2=H$;

e. $R_1=H$, $R_2=OSi(Me)_2t$—$C_4H_9$;

f. $R_1=CH_3$, $R_2=OSi(Me)_2t$—$C_4H_9$.

13. A process of claim 10 wherein X=p-fluorobenzyloxy.

14. A process of claim 13 wherein the compound (III) prepared is selected from the group wherein:

a. $R_1=CH_3$, $R_2=H$;

b. $R_1=CH_2OSi(Me)_2t$—$C_4H_9$, $R_2=H$;

c. $R_1=H$, $R_2=CH_2OSi(Me)_2t$—$C_4H_9$;

d. $R_1=OSi(Me)_2t$—$C_4H_9$, $R_2=H$;

e. $R_1=H$, $R_2=OSi(Me)_2t$—$C_4H_9$;

f. $R_1=CH_3$, $R_2=OSi(Me)_2t$—$C_4H_9$.

15. A process of claim 7 wherein the catalyst is 1,5-cyclooctadiene(pyridine)(tricyclohexylphosphine)iridium(I)hexafluorophosphate and the solvent is a mixture of dichloromethane and isopropanol.

16. A process of claim 9 wherein the catalyst is 1,5-cyclooctadiene(pyridine)(tricyclohexylphosphine)iridium(I)hexafluorophosphate and the solvent is a mixture of dichloromethane and isopropanol.

17. A process of claim 12 wherein the catalyst is 1,5-cyclooctadiene(pyridine)(tricyclohexylphosphine)iridium(I)hexafluorophosphate and the solvent is a mixture of dichloromethane and isopropanol.

18. A process of claim 14 wherein the catalyst is 1,5-cyclooctadiene(pyridine)(tricyclohexylphosphine)iridium(I)hexafluorophosphate and the solvent is a mixture of dichloromethane and isopropanol.

* * * * *